US010155062B2

(12) United States Patent
Dalal et al.

(10) Patent No.: US 10,155,062 B2
(45) Date of Patent: Dec. 18, 2018

(54) THERMORESPONSIVE ADHESIVE MATERIAL, METHOD OF MAKING THE MATERIAL AND METHODS OF USE

(71) Applicant: The Boeing Company, Chicago, IL (US)

(72) Inventors: Hardik Dalal, Seattle, WA (US); Alain A. Adjorlolo, Shoreline, WA (US); Adam F. Gross, Santa Monica, CA (US); Elena Sherman, Culver City, CA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/163,365

(22) Filed: May 24, 2016

(65) Prior Publication Data

US 2017/0340769 A1 Nov. 30, 2017

(51) Int. Cl.
*A61L 15/58* (2006.01)
*C09J 5/06* (2006.01)
(Continued)

(52) U.S. Cl.
CPC ............ *A61L 15/58* (2013.01); *C08F 220/24* (2013.01); *C09J 5/06* (2013.01); *C09J 7/22* (2018.01);
(Continued)

(58) Field of Classification Search
CPC ...... A61L 15/58; C09J 7/38; C09J 7/22; C09J 5/06; C09J 133/16; C09J 2477/006;
(Continued)

(56) References Cited

U.S. PATENT DOCUMENTS 5,106,383 A 4/1992 Mulder et al.
5,470,622 A * 11/1995 Rinde ................ B29C 61/0616 156/84

(Continued)

FOREIGN PATENT DOCUMENTS

JP 2012011656 A 1/2012

OTHER PUBLICATIONS

De Crevoisier et al. (Switchable Tackiness and Wettability of a Liquid Crystalline Polymer).*

(Continued)

*Primary Examiner* — Aradhana Sasan
*Assistant Examiner* — Quanglong N Truong
(74) *Attorney, Agent, or Firm* — MH2 Technology Law Group LLP

(57) ABSTRACT

The present disclosure is directed to a thermoresponsive adhesive material. The material comprises a linear, phase-separated polymer having fluorinated polymer units and hydrophobic polymer units. The fluorinated polymer units and the hydrophobic polymer units are randomly ordered along the polymer. The hydrophobic polymer units include a first hydrophobic polymer unit and a second hydrophobic polymer unit. The first hydrophobic polymer unit is chosen from acrylate units or methacrylate units each substituted with one or more linear alkyl groups, linear alkenyl groups or a combination thereof, where at least one of the linear alkyl groups or alkenyl groups has 16 to 20 carbon atoms. The second hydrophobic polymer unit is chosen from acrylate units or methacrylate units each substituted with one or more linear alkyl groups, linear alkenyl groups or a combination thereof, where at least one of the linear alkyl or alkenyl groups of the second hydrophobic polymer unit has 5 to 14 carbon atoms. A peak adhesive strength of the thermoresponsive adhesive material is modifiable and
(Continued)

108
106
102
104
110
108
106
102 reversible with a change in temperature. Methods of making thermoresponsive adhesive materials, methods employing thermoresponsive adhesive materials and self-adhesive objects that include thermoresponsive adhesive materials are also disclosed.

29 Claims, 5 Drawing Sheets

(51) Int. Cl.
*C09J 133/16* (2006.01)
*C08F 220/24* (2006.01)
*C09J 7/38* (2018.01)
*C09J 7/22* (2018.01)

(52) U.S. Cl.
CPC ............... *C09J 7/38* (2018.01); *C09J 133/16* (2013.01); *C09J 2205/114* (2013.01); *C09J 2423/006* (2013.01); *C09J 2423/046* (2013.01); *C09J 2423/106* (2013.01); *C09J 2433/00* (2013.01); *C09J 2467/006* (2013.01); *C09J 2477/006* (2013.01)

(58) Field of Classification Search
CPC ............ C09J 2423/106; C09J 2423/046; C09J 2205/114; C09J 2433/00; C09J 2467/006; C09J 2423/006; C08F 220/24
See application file for complete search history.

(56) References Cited

U.S. PATENT DOCUMENTS

| | | | |
|---|---|---|---|
| 2010/0186889 | A1 | 7/2010 | Kipp et al. |
| 2011/0143134 | A1 | 6/2011 | Emslander et al. |
| 2011/0198785 | A1 | 8/2011 | Kester et al. |
| 2012/0121866 | A1 | 5/2012 | Hawkins et al. |
| 2013/0174396 | A1 | 7/2013 | Torres Martinez |
| 2014/0284836 | A1 | 9/2014 | Kline et al. |
| 2016/0001464 | A1 | 1/2016 | Suzuki |
| 2016/0059443 | A1 | 3/2016 | Thomas et al. |
| 2016/0068727 | A1 | 10/2016 | Nanchi et al. |

OTHER PUBLICATIONS

De Crevoisier et al. (Structure of Fluorinated Side-Chain Smectic Copolymers: Role of the Copolymerization Statistics).*

Guillaume De Crevoisier et al., “Switchable Tackiness and Wettability of a Liquid Crystalline Polymer”, Science, vol. 285, Aug. 20, 1999, pp. 1246-1249.

G. De Crevoisier et al., “Structure of Fluorinated Side-Chain Smectic Copolymers: Role of the Copolymerization Statistics”, Macromolecules, 35, 2002, pp. 3880-3888.

Hardik Dalal et al., “Method for Pre-Preg Manufacturing”, U.S. Appl. No. 15/163,180, filed May 24, 2016.

ThomasNet, “Pressure Sensitive Adhesive,” <https://www.thomasnet.com/articles/adhesives-sealants/pressure-sensitive-adhesives/> (Available May 23, 2010, Retrieved Jan. 19, 2018.

Choi, “Adhesion Properties of Styrene-Butadiene-Styrene Triblock Copolymer-Based Pressure-Sensitive Adhesives for Protecting Opto-Functionalized Sheets,” Asian Journal of Chemistry; vol. 25, No. 9 (2013), 5233-5236.

Material Property Data: Kraton D1192E Linear Block Copolymer, Feb. 1, 2018.

Holden. Thermoplastic Elastomer, Encyclopedia of Polymer Science and Technology, 2010.

Ruffato et al., “Improving Controllable Adhesion on Both Rough and Smooth Surfaces With a Hybrid Electrostatic/Gecko-Like Adhesive,” 2014, J.R. Soc. Interface 11:20131089. http://dx.doi.org/10.1098/rsif.2013.1089.

Author Unknown, Glossary of Terms, Pressure Sensitive Tape Council, PSTC, http://www.pstc.org/i4a/pages/index.cfm?pageID=3336%281%20pp%29, accessed May 23, 2016, pp. 1-6.

Extended European Search Report dated Nov. 8, 2017 from related European Application No. 17167672.8.

* cited by examiner

THERMORESPONSIVE ADHESIVE MATERIAL, METHOD OF MAKING THE MATERIAL AND METHODS OF USE

DETAILED DESCRIPTION

Field of the Disclosure

The present disclosure is directed to a novel thermoresponsive adhesive material and methods of using the material, including a pre-preg molding process that uses the material for manufacturing composite parts.

Background

Thermoresponsive adhesive materials that have reversible, temperature dependent adhesive properties are known in the art. One example is shown in an article entitled, "Switchable Tackiness and Wettability of a Liquid Crystalline Polymer," Science, 1999, 285, 1246-1249, authored by Guillaume de Crevoisier, et al. In the Crevoisier et al. paper, the authors show that a fluorinated-hydrophobic phase-separated polymer changes tack with temperature.

In the field of composite part manufacturing, composite parts are often manufactured using pre-impregnated composite fibers, also known as "pre-preg". Pre-preg employs a matrix material, such as epoxy, that is already present in a fiber reinforcement before molding of the composite occurs. Prep-reg manufacturing techniques are often employed to manufacture composite parts for a variety of commercial uses, including the manufacture of aircraft, for example. Composite part manufacturing using pre-preg techniques can be a rate limiting step in the production rates of composite products.

In conventional composite part manufacturing techniques, pre-preg is laid up on polymer parting film that covers a mold. The parting film is composed of a non-adhesive polymer sheet. The parting film is replaced each time a composite part is made on a mold in current practices, which consumes manufacturing time and creates material waste. Furthermore, in order to enable easy release of pre-preg, the adhesion between the pre-preg and parting film is low. Due to the low adhesion, the pre-preg may slip around on the surface during placement and thereby consume additional time.

There is a need in the art for novel materials and techniques that can provide improved efficiency in manufacturing processes, such as in the manufacture of pre-preg composites.

SUMMARY

The present disclosure is directed to a thermoresponsive adhesive material. The material comprises a linear, phase-separated polymer having fluorinated polymer units and hydrophobic polymer units. The fluorinated polymer units and the hydrophobic polymer units are randomly ordered along the polymer. The hydrophobic polymer units include a first hydrophobic polymer unit and a second hydrophobic polymer unit. The first hydrophobic polymer unit is chosen from acrylate units or methacrylate units each substituted with one or more linear alkyl groups, linear alkenyl groups or a combination thereof, where at least one of the linear alkyl groups or alkenyl groups has 16 to 20 carbon atoms. The second hydrophobic polymer unit is chosen from acrylate units or methacrylate units each substituted with one or more linear alkyl groups, linear alkenyl groups or a combination thereof, where at least one of the linear alkyl or alkenyl groups of the second hydrophobic polymer unit has 5 to 14 carbon atoms. A peak adhesive strength of the thermoresponsive adhesive material is modifiable and reversible with a change in temperature.

The present disclosure is also directed to a method of making a thermoresponsive adhesive material. The method comprises combining at least one fluorinated monomer, a first hydrophobic monomer, and a second hydrophobic monomer and heating the monomers to form a linear, phase-separated polymer. The at least one fluorinated monomer is chosen from acrylates or methacrylates each substituted with fluorinated alkyl groups. The first hydrophobic monomer is chosen from acrylates or methacrylates substituted with at least one linear alkyl group, linear alkenyl group or a combination thereof, at least one alkyl or alkenyl group having 16 to 20 carbon atoms. The second hydrophobic monomer is chosen from acrylates or methacrylates substituted with at least one linear alkyl group, linear alkenyl group or a combination thereof, at least one alkyl or alkenyl group of the second hydrophobic monomer having 5 to 14 carbon atoms. A peak adhesive strength of the thermoresponsive adhesive material is modifiable and reversible with a change in temperature.

The present disclosure is also directed to a method comprising covering a mold tool for a composite part with a parting film. The parting film comprises a polymer sheet and a thermoresponsive adhesive material on the polymer sheet. The thermoresponsive adhesive material has a property of changing adhesion with a change in temperature. The parting film is positioned so that the polymer sheet is between the mold tool and the thermoresponsive adhesive material. The method further includes laying up at least one layer of pre-preg on the parting film covering the mold tool to form a composite part, the pre-preg comprising an adhesive surface in contact with the thermoresponsive adhesive material, the thermoresponsive adhesive material resulting in the at least one layer of pre-preg adhering to the parting film with a first adhesion force while laying up occurs; changing the temperature of the thermoresponsive adhesive material from a first temperature to a second temperature to modify the first adhesion force to a second adhesion force that is less than the first adhesion force; and removing the composite part from the parting film.

The present disclosure is directed to a method comprising adhering a first object to a second object with a thermoresponsive adhesive material. The thermoresponsive adhesive material has a property of changing adhesion with a change in temperature. The thermoresponsive adhesive material results in the first object adhering to the second object with a first adhesion force. The method further includes changing the temperature of the thermoresponsive adhesive material from a first temperature to a second temperature to reduce the adhesion between the second object and the thermoresponsive adhesive material to a second adhesion force, the second adhesion force being less than the first adhesion force; and removing the first object from the second object. The thermoresponsive adhesive material comprises a linear, phase-separated polymer having fluorinated polymer units and hydrophobic polymer units. The fluorinated polymer units and the hydrophobic polymer units are randomly ordered along the polymer. The hydrophobic polymer units include a first hydrophobic polymer unit and a second hydrophobic polymer unit. The first hydrophobic polymer unit is chosen from acrylate units or methacrylate units each substituted with one or more linear alkyl groups, linear alkenyl groups or combinations thereof, where at least one of the linear alkyl or alkenyl groups has 16 to 20 carbon atoms. The second hydrophobic polymer unit is chosen from acrylate units or methacrylate units each substituted with one or more linear alkyl groups, linear alkenyl groups or combinations thereof, where at least one of the linear alkyl or alkenyl groups of the second hydrophobic polymer unit has 5 to 14 carbon atoms.

The present disclosure is directed to a self-adhesive object. The object comprises a flexible substrate; and a thermoresponsive adhesive material layer on the substrate, the thermoresponsive adhesive material having a property of changing adhesion with a change in temperature. The thermoresponsive adhesive material can have variable adhesion when in contact with another adhesive material. The thermoresponsive adhesive material comprises a linear, phase-separated polymer having fluorinated polymer units and hydrophobic polymer units, the fluorinated polymer units and the hydrophobic polymer units being randomly ordered along the polymer. The hydrophobic polymer units include a first hydrophobic polymer unit and a second hydrophobic polymer unit, the first hydrophobic polymer unit being chosen from acrylate units or methacrylate units each substituted with one or more linear alkyl groups, linear alkenyl groups or a combination thereof, where at least one of the linear alkyl or alkenyl groups has 16 to 20 carbon atoms. The second hydrophobic polymer unit is chosen from acrylate units or methacrylate units each substituted with one or more linear alkyl groups, linear alkenyl groups or a combination thereof, where at least one of the linear alkyl or alkenyl groups of the second hydrophobic polymer unit has 5 to 14 carbon atoms.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrates aspects of the present teachings and together with the description, serve to explain the principles of the present teachings.

Figure 1A:
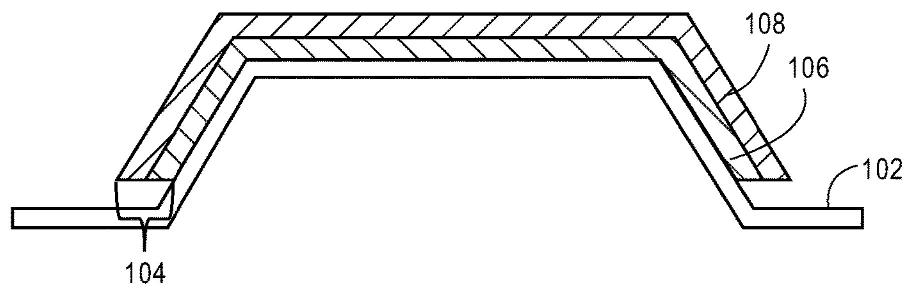
FIG. 1A shows a method for manufacturing a composite part using a pre-preg manufacturing technique, according to an aspect of the present disclosure.

It should be noted that some details of the figures have been simplified and are drawn to facilitate understanding rather than to maintain strict structural accuracy, detail, and scale.

DESCRIPTION

Reference will now be made in detail to the present teachings, examples of which are illustrated in the accompanying drawings. In the drawings, like reference numerals have been used throughout to designate identical elements. In the following description, reference is made to the accompanying drawings that form a part thereof, and in which is shown by way of illustration specific examples of practicing the present teachings. The following description is, therefore, merely exemplary.

The present disclosure is directed to a thermoresponsive adhesive material that exhibits tunable, reversible adhesive properties. The thermoresponsive adhesive material comprises a linear, phase-separated polymer having fluorinated polymer units and hydrophobic polymer units. The polymer units are randomly ordered along the polymer chain in a manner that allows units of the same type to group together. The size of the monomer groupings are small, possibly about 1 nm to about 20 nm, or about 5 nm to about 10 nm, and may be outside of these ranges as long as they are sufficiently sized so as to allow for a crystalline to amorphous phase change that results in changes in adhesion with relatively small drops in temperature. This phase change will be discussed in more detail below. The monomer groupings may, in part, be achieved by bending of the linear polymer chains to allow randomly arranged monomers of the same type to gather together. Thus, the phase-separated polymers are considered random copolymers, not block polymers, by those of ordinary skill in the art.

The phase-separated polymers of the present disclosure can have a broad range of molecular weights. As an example, the molecular weight can range from 2000 to 20,000 g/mol. The molecular weight distribution can have a single peak or be multimodal. For instance, the phase-separated polymers can have a bimodal molecular weight distribution. An example range for bimodal molecular weight distributions include a first maxima centered within the range of 5000 to 7000 g/mol, such as 5500 to 6500 g/mol, and a second distribution centered at 9500 to 11,500 g/mol, such as 10,000 to 11,000 g/mol, relative to polystyrene molecular weight standards. All molecular weight values herein are weight average molecular weights unless otherwise stated.

The tackiness, or adhesive nature of the thermoresponsive adhesive material is modifiable and reversible with a change in temperature. This is largely due to the ability of the phase-separated polymer to switch with changes in temperature between a crystalline state and an amorphous state. The crystalline state, which may be, for example, a smectic phase, is achieved at relatively low temperatures at which the hydrocarbon is generally hard and non-adhesive. When the temperature is raised sufficiently so that the polymer switches to the amorphous state, which in some cases may be considered an isotropic phase, the hydrocarbon becomes relatively soft and conformable with an associated increase in tackiness, or adhesion.

The fluorinated polymer units of the phase-separated polymer of the present disclosure provide a low adhesion material that is bound together by the potentially more adhesive hydrophobic monomer material. Thus, as the relative amount of fluorinated monomer in the polymer increases, the maximum adhesion of the polymer decreases, and vice versa.

The fluorinated polymer can include any suitable polymer units that can reduce adhesion and that will work with the hydrophobic units to exhibit the desired shift between the crystalline phase and the amorphous phase. Suitable fluorinated polymer units include fluorinated acrylate or methacrylate groups derived from corresponding fluoro-alkyl acrylate or fluoro-alkyl methacrylate monomers. The alkyl substituent of the acrylate or methacrylate groups is a fluorinated alkyl having 5 to 12 carbon atoms. Examples of suitable monomers include acrylates or methacrylates substituted with fluorinated alkyl groups, such as those of Formula 1 or 2:

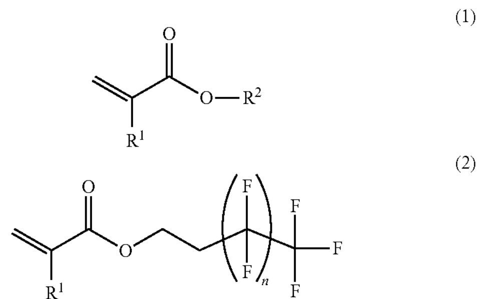

Where $R^1$ can be a hydrogen or methyl group; $R^2$ can be a fluoro alkyl having 6 to 20 carbon atoms, such as 8 to 12 carbon atoms, where the ratio of fluorine to hydrogen atoms on the $R^2$ group is at least 1:1, such 2:1 to 10:1. In an example, the $R^2$ group can be perfluorinated (100% fluorine substitution). Formula 2 shows an example, where n can range from 3 to 17, such as 5 to is 11. In yet another example, the monomer can be 1H,1H,2H,2H-Heptadecafluorodecyl methacrylate.

Suitable hydrophobic units that will go through the crystalline to amorphous phase transition when combined with the fluorinated polymer units can potentially be used. As examples, suitable hydrophobic polymer units include acrylate units or methacrylate units each substituted with one or more linear alkyl groups, linear alkenyl groups or combinations thereof, where at least one of the linear alkyl or alkenyl groups has 16 to 20 carbon atoms, or 18 to 20 carbon atoms. As an example, the hydrophobic polymer units are acrylate units substituted with a stearyl group. The hydrophobic polymer units can be derived from suitable corresponding acrylate or methacrylate monomers, including for example, acrylates or methacrylates substituted with at least one linear alkyl group, linear alkenyl group or a combination thereof, at least one alkyl or alkenyl group having 16 to 20 carbon atoms, as shown in the formula 3 shown below:

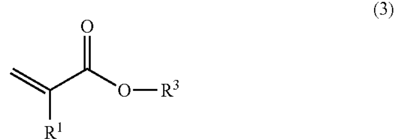

Where $R^1$ can be a hydrogen or methyl group and $R^3$ can be an alkyl or alkenyl having 16 to 20 carbon atoms. In an example, $R^3$ has 17 to 19 carbon atoms, such as 18 carbon atoms. With respect to 18 carbon atom groups, it was found by the inventors of the present disclosure that $C_{18}$ alkyl substituted monomers, such as octadecyl acrylate or stearyl methacrylate, work particularly well for applications where the switch between the low adhesion crystalline state and high adhesion amorphous state is desired to occur near room temperature. It is believed that phase transition temperature for the longer alkane groups would occur at temperatures much higher than room temperature, while alkane groups shorter than 18 carbon atoms (e.g., 16 carbon atoms) softened, and thus exhibited an amorphous to crystalline phase transition at temperatures far below room temperature.

Optionally, the hydrophobic polymer units can further include a second, hydrophobic group having an alkyl or alkenyl group of 5 to 14 carbon atoms, such as those formed from monomers of generic formula 4:

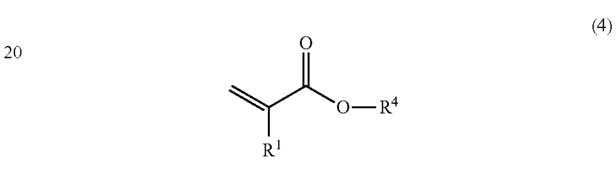

where $R^1$ is a hydrogen or methyl group and $R^4$ is an alkyl or alkenyl group having 5 to 14 carbon atoms, such as 8 to 13 carbon atoms, or 12 carbon atoms. These smaller molecular weight hydrophobic polymer units can be formed from, for example, $C_{10}$ to $C_{12}$ alkyl methacrylates, $C_{10}$ to $C_{12}$ alkyl acrylates, $C_{10}$ to $C_{12}$ alkenyl methacrylates, and $C_{10}$ to $C_{12}$ alkenyl acrylates. One such monomer is lauryl methacrylate. The use of such monomers having shorter alkyl groups in combination with the longer alkyl or alkenyl substituted hydrophobic monomers discussed above was found to decrease the temperature at which the polymer switched between the crystalline phase to the amorphous phase. Mixing the C18 alkyl or alkenyl substituted hydrophibic monomers with the shorter chain hydrophobic monomers allowed for polymers with crystalline-to-amorphous phase transitions that more closely approached room temperature than the polymers made with only the C18 hydrophobic monomers.

When discussing the polymer products of the present disclosure, it is to be understood that the name of a particular monomer followed by the term "unit", "polymer unit", "polymer unit" or "group" refers to a polymer unit formed from the corresponding monomer (e.g., a methacrylate unit or group is the portion of the polymer formed from the methacrylate monomer). Similarly, when discussing substituents of polymer units in the present disclosure, the substituent modified by the term "group" or "moiety" (e.g., "alkyl group" or "alkenyl moiety") refer to the portion of the polymer that was formed from that corresponding group or moiety in the monomer, and which may be the same or different from the alkyl group or moeity of the monomer. For example, an "alkyl group" of an acrylate polymer unit in the polymer can be an alkyl, an alkyl bridge, or some other group as long as it is the portion of the polymer formed from the corresponding alkyl of the acrylate monomer.

If the ratio of fluorinated monomers to hydrophobic monomers is too low, adhesion may not be sufficiently reduced in the crystalline phase to allow for an easy release of the adhesive material from the surface to which it is adhered. Alternatively, if the ratio is too high, sufficient adhesion may not be achieved in the amorphous phase. The particular monomer ratio employed can depend on a variety of factors, such as the desired strength of adhesion in the amorphous phase, the desired reduction in adhesion in the crystalline phase, the particular monomers being employed and the specific material to which the adhesive polymer material is designed to adhere. As an example, where an adhesive system is designed to have variable adhesion against pre-preg comprising an epoxy resin, the molar ratio of fluorinated monomers to hydrophobic monomers can range from about 35:65 to about 65:35, such as about 40:60 to about 60:40, or about 45:55 to about 55:45 moles of fluorinated monomer to moles of hydrophobic monomer. For an adhesive system designed to have variable adhesion against a material other than the pre-preg of the present disclosure, broader monomer molar ratios may be considered, such as 20:80 to about 80:20, or about 30:70 to about 70:30 moles of fluorinated monomer to moles of hydrophobic monomer.

The thermoresponsive adhesive materials of the present disclosure can be additive free, meaning that only the phase-separated polymer is employed as the adhesive. Alternatively, in addition to the phase-separated polymer described herein, the adhesive compositions of the present disclosure can optionally include any other suitable ingredients in any desired amounts, such as carrier liquids, plasticizers, tackifiers, pigments, levelling agents/surfactants and other such components to manage viscosity, adhesion strength, the ability to retain moisture content over time, and other desired properties. Ingredients not expressly recited in the present disclosure can be limited and/or excluded from the thermoresponsive adhesive materials disclosed herein. Thus, the amounts of the thermoresponsive polymer and one or more of the disclosed optional ingredients, including carrier liquids, plasticizers, tackifiers, pigments, and leveling agents/surfactants, can add up to 90% to 100% by weight of the total ingredients employed in the adhesive compositions of the present disclosure, such as 95% to 100% by weight, or 98% to 100% by weight, or 99% to 100% by weight, or 100% by weight of the total ingredients.

As discussed above, the degree of adhesion exhibited by the thermoresponsive adhesive material can vary depending on, for example, the particular monomers used to make the polymer. In the amorphous (adhesive) phase, the polymers can exhibit a peak adhesive strength ranging from about 3 kPa to about 500 kPa peak adhesion force, such as about 5 kPa to about 150 kPa peak adhesion force, where the peak adhesion force is determined as describe herein with respect to FIG. 2. In the crystalline (non-adhesive) phase, the adhesive strength can be reduced, for example, by about 90% to about 100%, such as 95% to about 99.9%, relative to the adhesion in the amorphous phase.

The change in adhesion occurs over a relatively small change in temperature, such as about a 1° to about a 15° change, or about a 2° to about a 10° change, or about a 2° to about a 5° change in temperature, where degrees are in Celsius. This is desirable because it allows the change in adhesion to occur with only a modest drop in temperature during processing. For other conventional materials, such as wax or most thermoplastic polymers, similar changes in adhesion occur over much larger temperature ranges, such as 50° C. or more.

As discussed herein, the precise temperature range over which the reduction in adhesion occurs can be adjusted to some degree by adjusting the length of the alkyl or alkenyl groups of the hydrophobic monomers. As an example, the reduction in adhesion can occur at temperatures ranging from about 15° C. to about 40° C., such as about 20° C. to about 36° C.

Any suitable method of making the thermoresponsive adhesive material can be employed. For example, at least one fluorinated monomer and at least one hydrophobic monomer can be combined in a solvent with heating to form a linear, phase-separated polymer having randomly arranged fluorinated polymer units and hydrophobic polymer units. Any of the fluorinated monomers or hydrophobic monomers discussed herein can be employed. The polymer reaction can be initiated by the addition of a polymerization initiator, such as, for example, 2,2'-azobis(2-methylpropionitrile); 2,2'-azobis(2-amidinopropane) hydrochloride, or 2,2'-azobis (isobutyronitrile).

Figure 1B:
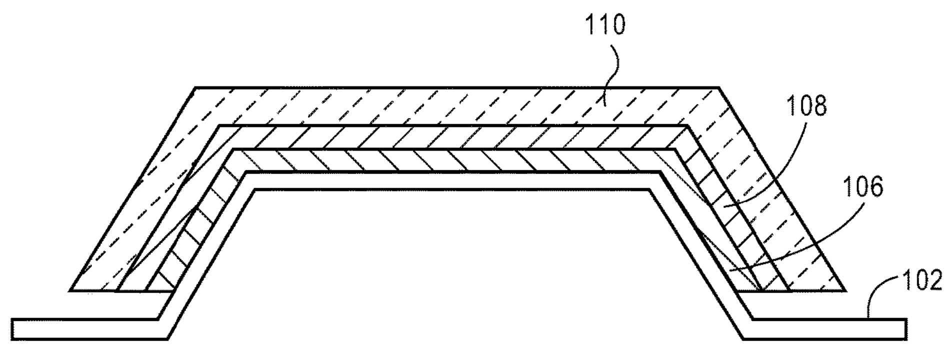
FIG. 1B shows the continued method of FIG. 1A for manufacturing a composite part using a pre-preg manufacturing technique, according to an aspect of the present disclosure.
Figure 1C:
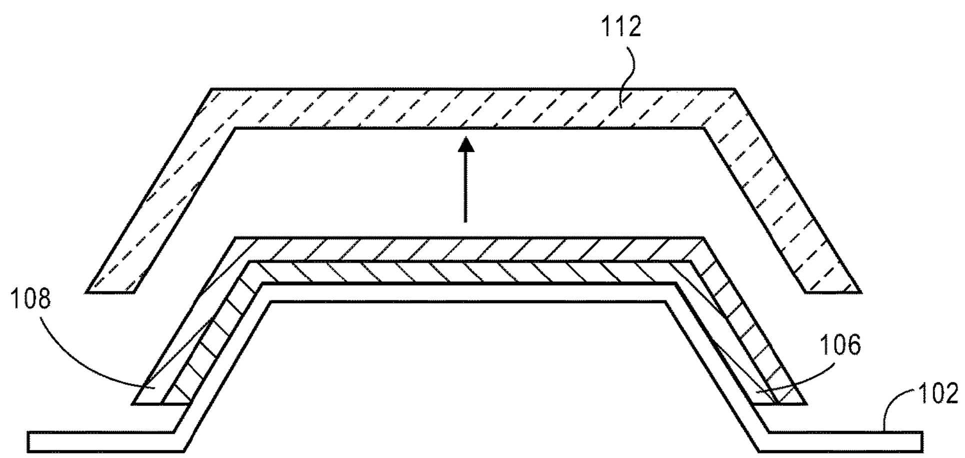
FIG. 1C shows the continued method of FIGS. 1A and 1B for manufacturing a composite part using a pre-preg manufacturing technique, according to an aspect of the present disclosure.

The present disclosure is also directed to a method for manufacturing a composite part using pre-preg manufacturing techniques. Referring to FIGS. 1A to 1C, the method involves covering a surface of mold tool 102 with a parting film 104 comprising a polymer sheet 106 and a thermoresponsive adhesive material 108. The thermoresponsive adhesive material can be in any suitable form, such as a layer deposited on or otherwise attached to the polymer sheet 106. The thickness of the thermoresponsive adhesive material 108 on the polymer sheet 106 can range, for example, from 0.0001 to 0.01 inches, such as 0.001 to 0.004 inches, or 0.001 to 0.002 inches. The thermoresponsive adhesive material has the property of changing adhesion with a change in temperature. The parting film 104 is positioned so that the polymer sheet 106 is between the mold tool 102 and the thermoresponsive adhesive material 108. Referring to FIG. 1B, at least one layer of pre-preg 110 is layed up on the parting film covering the mold tool to form a layed up composite part 112. As shown in FIG. 1C, after the lay up process is complete, the molded composite part 112 is removed from the parting film 104. The laying up step of FIG. 1B and the removing step of FIG. 1C can optionally be repeated a desired number of times, such as one or a plurality of times, to form a desired number of composite parts 112 without removing the parting film 104 from the mold tool 102. As an example, the laying up step and the removing step can be carried out 5 to 50 times, such as 10 to 30 times or 15 to 25 times without removing the parting film 104.

The polymer sheet 106 can comprise any polymer material that is non-adhesive to the pre-preg 110 and that has the structural ability to act as a standalone substrate, conform to the mold surface and withstand other pre-preg processing conditions. The polymer sheet 106 generally does not contain acrylics, rubber, styrene-butadiene-styrene copolymers or other styrene copolymers. For example, suitable non-adhesive polymer sheets can comprise a material chosen from polyethylene, polyethylene terephthalate ("PET"), fluorinated ethylene propylene ("FEP"), nylon and combinations thereof. The thickness of the polymer sheet 106 can range, for example, from 0.0001 to 0.01 inches, such as 0.001 to 0.004 inches.

Any suitable thermoresponsive adhesive material can be employed in the methods of the present disclosure. As an example, any of the thermoresponsive materials disclosed herein can be used as the thermoresponsive adhesive material 108. The thermoresponsive adhesive material is chosen to have the property of adhering to the pre-preg 110 sufficiently to significantly reduce slipping during lay up while, at the same time, having the ability to release the composite part 112 after lay-up is complete, without damaging the composite part (e.g., without pulling out carbon fiber or transferring material to pre-preg so as to change the composite part properties in an undesirable manner).

The thermoresponsive adhesive material can be coated onto the polymer sheet 106 using any suitable coating techniques for polymer deposition. A variety of suitable polymer coating techniques are known in the art. If desired, the polymer sheet can be plasma-treated prior to coating to improve adhesion between the non-adhesive polymer material and the thermoresponsive adhesive material 108. Any suitable plasma treatment techniques for improving adhesion can be used. Techniques for plasma treating polymer films and other substrates are generally well known in the art. For example, corona treatment is a suitable plasma technique that is well known for use in film coating production lines. Such treatment can be used to form a corona-treated polymer sheet to improve adhesion.

The pre-preg 110 used to manufacture the composite part in the process of FIGS. 1A to 1C can be any suitable pre-preg. Pre-preg materials are well known in the art and generally comprise fibers in an adhesive resin. As an example, the pre-preg can comprise a carbon fiber reinforced plastic and/or one or more epoxy chemical groups that effectively act as an adhesive for adhering multiple pre-preg layers together. The epoxy of the pre-preg can also potentially adhere to other materials, such as the thermoresponsive adhesive material 108 of the parting film. As an example, the epoxy based pre-preg employed in the processes of the present disclosure can be said to have a threshold adhesive strength against a steel plate of greater than 10 kPa, such as about 30 to about 120 kPa, where the adhesive strength is measured using the tack test as described below with respect to FIG. 2, except that the steel probe is used without attaching a parting film 104.

During the lay up process, the thermoresponsive adhesive material 108 can allow the at least one layer of pre-preg 110 to adhere to the parting film 104. However, during the removal step of FIG. 1C, the adhesive force holding the composite part 112 to the thermoresponsive adhesive material 108 can be reduced by changing the temperature of the thermoresponsive adhesive material from a first temperature to a second temperature. The change in temperature modifies the adhesion so that a second adhesion force exists between the composite part and the parting film 104, where the second adhesion force is less than the first adhesion force. The reduction in peak adhesion force realized between the pre-preg and the thermoresponsive adhesive material when the temperature is reduced can range from 90% less to 100% less than the first adhesion force. In an example, the reduced adhesion is close to or at zero adhesion.

The precise temperature at which the reduction in adhesive force can be realized, as well as the number of degrees that the temperature changes before the desired reduction is realized, will depend on such things as the precise formulation of the thermoresponsive adhesive material 108 and the desired degree of reduction in adhesion. As an example, the reduction in temperature can be about 4 to about 15 degrees Celsius cooler than the temperature at which the composite is layed up.

The use of the thermoresponsive adhesive material to reversibly adhere to another adhesive surface, such as pre-preg, is believed to be a novel aspect of the present disclosure. The thermoresponsive adhesive materials of the present disclosure can reduce adhesion to at or near zero while being pressed against another adhesive material (e.g., the resin in pre-preg).

Referring again to FIG. 1C, removal of the layed up composite part 112 can be performed in any suitable manner after reduction of the adhesive force. For example, removal can be performed with a tool that adheres to the composite part, such as a vacuum chuck or other robotic device or by hand.

After removal of the composite part from the mold, little or no thermoresponsive adhesive material remains on the composite layer. As an example, 0 to about 30 micrograms/$cm^2$ of the thermoresponsive adhesive material 108 remains on a surface 114 of the completed part that was in contact with the thermoresponsive adhesive material 108 during laying up of the pre-preg 110. As another example, 0 to 20 micrograms/$cm^2$, such as 0 to 5 micrograms/$cm^2$ or 0 to 12 microgram/$cm^2$, of the thermoresponsive adhesive material 108 remains on the surface 114 of the completed part that was in contact with the parting film during laying up of the pre-preg 110. The amount of residue can be determined using the residue analysis procedure as described in Example 4 below.

While the thermoresponsive adhesive material 108 has been disclosed above for use with a pre-preg mold process, the thermoresponsive adhesive materials of the present disclosure can be used in any other application for which a reduction in adhesion in response to a change in temperature is useful. Thus, a more generic method of the present disclosure comprises: adhering a first object to a second object with a thermoresponsive adhesive material, the thermoresponsive adhesive material having the property of changing adhesion with a change in temperature, the thermoresponsive adhesive material resulting in the first object adhering to second object with a first adhesion force; changing the temperature of the thermoresponsive adhesive material from a first temperature to a second temperature to reduce the adhesion between the second object and the thermoresponsive adhesive material to a second adhesion force, the second adhesion force being less than the first adhesion force; and removing the first object from the second object. Any of the thermoresponsive adhesive materials of the present disclosure can be employed in this generic method.

Figure 5:
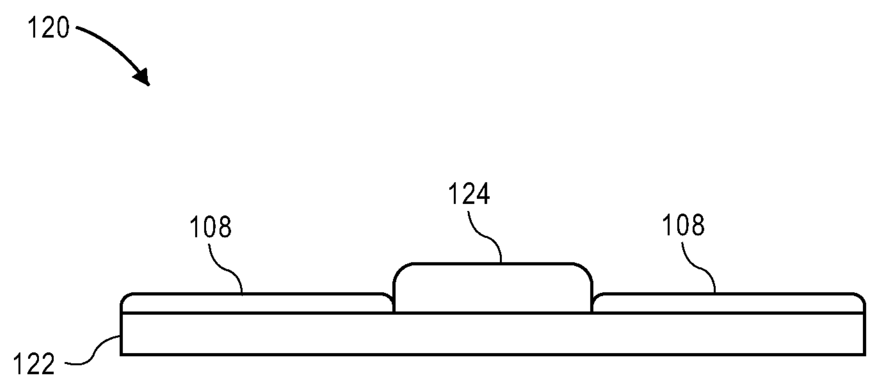
FIG. 5 shows an example of a self-adhesive object, according to the present disclosure.

The present disclosure is also directed to a self-adhesive object 120, as shown in FIG. 5. The self-adhesive object comprises a substrate 122 and a thermoresponsive adhesive material 108 on the substrate 122. Substrate 122 can comprise any suitable flexible or non-flexible material. The thermoresponsive adhesive material 108 has a property of changing adhesion with a change in temperature and can comprise any of the thermoresponsive adhesive materials described herein. The thermoresponsive adhesive material can be in any suitable form, such as a layer deposited on or otherwise attached to the substrate 122. The thermoresponsive adhesive material 108 can have any desired thickness on the substrate 122, including any thickness or range of thicknesses disclosed herein for the thermoresponsive adhesive material 108. The self-adhesive object 120 can be an adhesive bandage, as shown in FIG. 5. The bandage can optionally include one or more dressing materials 124 for treating a wound. A wide variety of dressing materials are contemplated, including medicated or non-medicated materials, such as gauze or any other synthetic or natural dressing materials. The bandage can adhere to a person at relatively warm temperatures, and can be removed from the person by exposing the bandage to a cold source, such as cold water or an ice cube. While the self-adhesive object is shown as a bandage in FIG. 5, a variety of self-adhesive objects are contemplated. Another example of a self-adhesive object is the parting film 104, as described above.

The thermoresponsive adhesive material can adhere to a variety of different surface types, including paper, plastic, glass, wood, cement and metal, upon mere contact, without the need of more than 20 pounds per square inch of pressure being applied. The thermoresponsive adhesive material requires no activation by water or solvent in order to exert a strong adhesive holding force toward such materials assuming the temperature of the polymer is sufficiently high to achieve the amorphous phase. Once the material is cooled sufficiently to reduce adhesion, it can be removed relatively easily without leaving a large amount of residue. As described herein, the reduced peak adhesion force exhibited at temperatures sufficiently low to achieve the crystalline phase is 90% less to 100% less than the adhesion force that exists when the polymer is above the amorphous-to-crystalline phase transition temperature.

EXAMPLES

Example 1

Polymer Synthesis

The fluorinated-hydrophobic phase-separated polymers of the following examples were synthesized by combining stearyl methacrylate (3.38 g, 10 mmol) and 1H,1H,2H,2H-Heptadecafluorodecyl methacrylate (5.32 g, 10 mmol) in 50 ml of butyl acetate. The system was deoxygenated by N2 bubbling for 30 minutes while stirring at 70° C. Polymerization was initiated by the addition of 0.174 g of 2,2'-azobis (2-methylpropionitrile) dissolved in 1 ml of butyl acetate. The reaction was carried out for 6 hours. To terminate the reaction, the mixture was cooled to ambient temperature and product was recovered by precipitation in large amounts of acetone (700 ml). The resulting phase-separated copolymers were washed with ethanol and dried. The phase-separated copolymers had a bimodal molecular weight distribution centered at 5998 and 10414 g/mol relative to polystyrene molecular weight standards.

Multiple versions of the fluorinated-hydrophobic phase-separated polymer were synthesized using similar techniques as those described above by varying the relative amounts of fluorinated monomers to hydrophobic monomers. All polymers are described in Table 1 below using the ratio XX/YY where XX is the molar amount of fluorinated monomers and YY is the molar amount of hydrophobic monomers. Initially, materials using a perfluorooctyl group (F8) and a $C_{18}$ (18 carbon long) hydrophobic monomer were formed. The transition temperature between low and high tack of the 50/50 thermoresponsive polymer was 36° C. and the transition temperature between low and high tack of the 30/70 thermoresponsive polymer was 35° C. These measurements were made using differential scanning calorimetry (DSC) and an endothermic peak was observed for the phase transition.

Example 2

Sample Preparation and Adhesion Properties

Films of fluorinated-hydrophobic phase-separated polymer were coated both onto steel and onto PET parting films. The coating process included making a solution of the phase-separated polymers of Example 1 at a concentration of 10 wt % polymer in butyl acetate. The coating solution was either 1) sprayed on steel or PET or 2) a 10 mil draw down bar was used to apply a uniform film of polymer solution on steel or PET and then the solvent was allowed to evaporate.

TABLE 1

Thermoresponsive tack of fluorinated-hydrophobic phase-separated polymer against steel and pre-preg.

| Testing temperature | 30/70 polymer on steel (adhesive strength/adhesion energy) | 30/70 polymer on pre-preg (adhesive strength/adhesion energy) | 50/50 polymer on steel (adhesive strength/adhesion energy) | 50/50 polymer on pre-preg (adhesive strength/adhesion energy |
|---|---|---|---|---|
| 25° C. | 0/0 | 0/0 | 0/0 | 0/0 |
| 36° C. | 25.8 kPa<br>0.7 uJ/cm$^2$ | 142.3 kPa<br>6.9 uJ/cm$^2$ | 0/0 | 113.3 kPa<br>3.3 uJ/cm$^2$ |
| 36° C. to 25° C. shift under compression | 7.7 kPa<br>0.2 uJ/cm$^2$ | 116.3 kPa<br>2.6 uJ/cm$^2$ | 0/0 | 0/0 |

Figure 2:
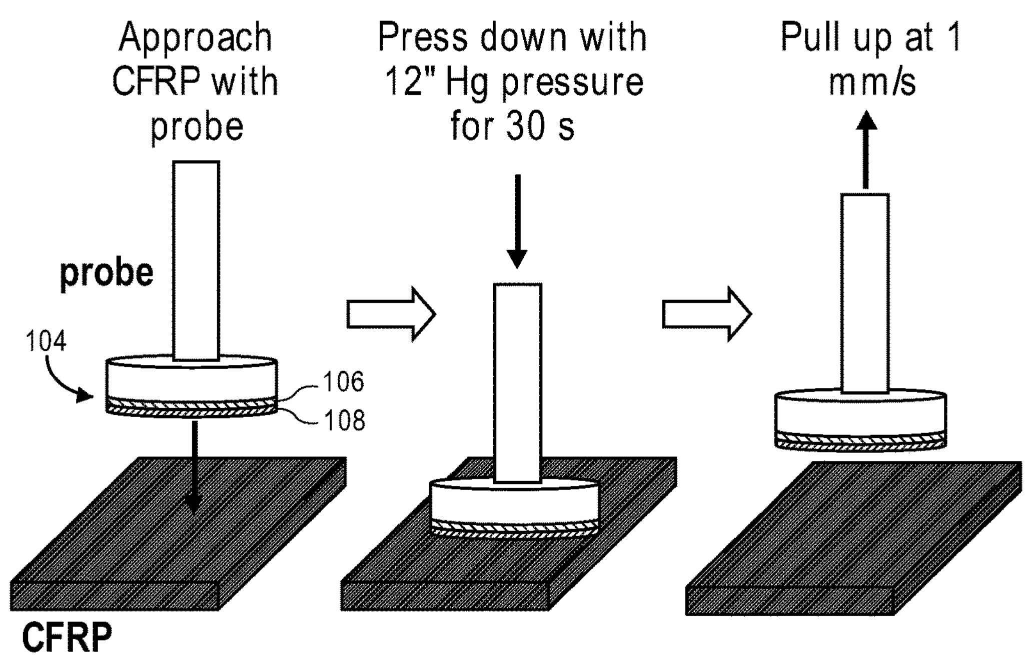
FIG. 2 is a schematic of a tack test, as described in the Examples below. A parting film coated with a tunable adhesion surface is attached to the bottom of the probe, with the tunable adhesion surface facing the pre-preg.

Mode 1 tack of the samples was measured using a Malvern Kinexus rheometer with a 0-50 N load cell. The experiment was performed by first attaching a parting film to a flat, 8 mm diameter steel probe and adhering pre-preg to the rheometer bottom plate. The pre-preg used for testing in the present disclosure was a Toray 3900-2/T800S type pre-preg comprising an intermediate modulus ("IM") carbon fiber and epoxy resin. The probe was brought down onto the sample, applying pressure equivalent to 12" of mercury on the sample with the probe for 30 seconds, and pulling up the probe at 1 mm/s. For testing a thermoresponsive adhesive material, the material was coated onto the parting film, which was then positioned on the probe so that the thermoresponsive adhesive material faced the pre-preg, and the pre-preg coated bottom flat plate was equilibrated at a set temperature for 5 minutes before bringing the probe into contact with the pre-preg. A schematic of the tack test is shown in FIG. 2.

Tack measurements of the example polymers against a steel probe and against pre-preg while in the low tack state (25° C.), high tack state (36° C.), and when the example polymer contacted the probe or pre-preg in the high tack state and the temperature was shifted to the low tack state before pulling the surfaces apart are shown in Table 1.

The 30/70 F8/$C_{18}$ sample shows significantly reduced adhesion against steel and a small reduction against pre-preg when the temperature was shifted from 36° C. to 25° C. while it was adhered. The 50/50 F8/$C_{18}$ showed a complete loss of adhesion when the temperature was shifted from 36° C. to 25° C. while it was adhered to pre-preg. Thus it fulfills the need to eliminate adhesion while in contact with another surface.

The tack measurement results of Table 1 provides evidence that a small difference in the number of carbon atoms in the hydrophobic group can have a significant impact on adhesion. In the Science article (Science, 1999, 285, 12-46-1249) it was shown that a 50/50 hydrophobic/fluorinated monomer mole ratio polymer showed variable adhesion to a rigid, non-conforming quart impactor when the hydrophobic monomer was a $C_{17}$ alkyl substituted acrylate. On the other hand, Table 1 shows that a similar 50/50 hydrophobic/fluorinated monomer mole ratio where the hydrophobic monomer was a $C_{18}$ alkyl substituted acrylate showed no adhesion to a rigid, non-conforming steel impactor in either a high or low temperature state. Thus, a single carbon atom change in length appears to have provided a relatively large difference in the adhesive characteristics of the material. Such a small change in alkyl length was not expected to show such a large difference in adhesion.

Example 3

Reduced Transition Temperature Samples

To reduce the transition temperature from high tack to low tack, two strategies were pursued: 1) shorter chain hydrocarbon monomers were used in place of $C_{18}$ and 2) much shorter chain hydrocarbon monomers were blended with the $C_{18}$ to form a material with an average lower alkyl length. The same procedures were followed as described above in Example 1.

When $C_{16}$ monomers were used instead of $C_{18}$ (strategy 1), the material was extremely soft and broke apart, thus the melting temperature was reduced too close to room temperature. Based on these results, it was determined that using all shorter chain hydrocarbon monomers than $C_{18}$ was not possible.

For strategy 2, $C_{12}$ monomers were blended with $C_{18}$ monomers. The first attempt of a 50/50 F8/(75% $C_{18}$+25% $C_{12}$) polymer melted at 27° C., which would undesirably result in transfer of material to pre-preg. Next, a 50/50 F8/(95% $C_{18}$+5% $C_{12}$) polymer was prepared with the idea that less $C_{12}$ would increase the melting point and, as expected, the tack transition decreased 2° C. (to 34° C.) from 100% $C_{18}$ and no polymer melting was observed in DSC measurements.

Example 4

Residue Analysis

Figure 3:
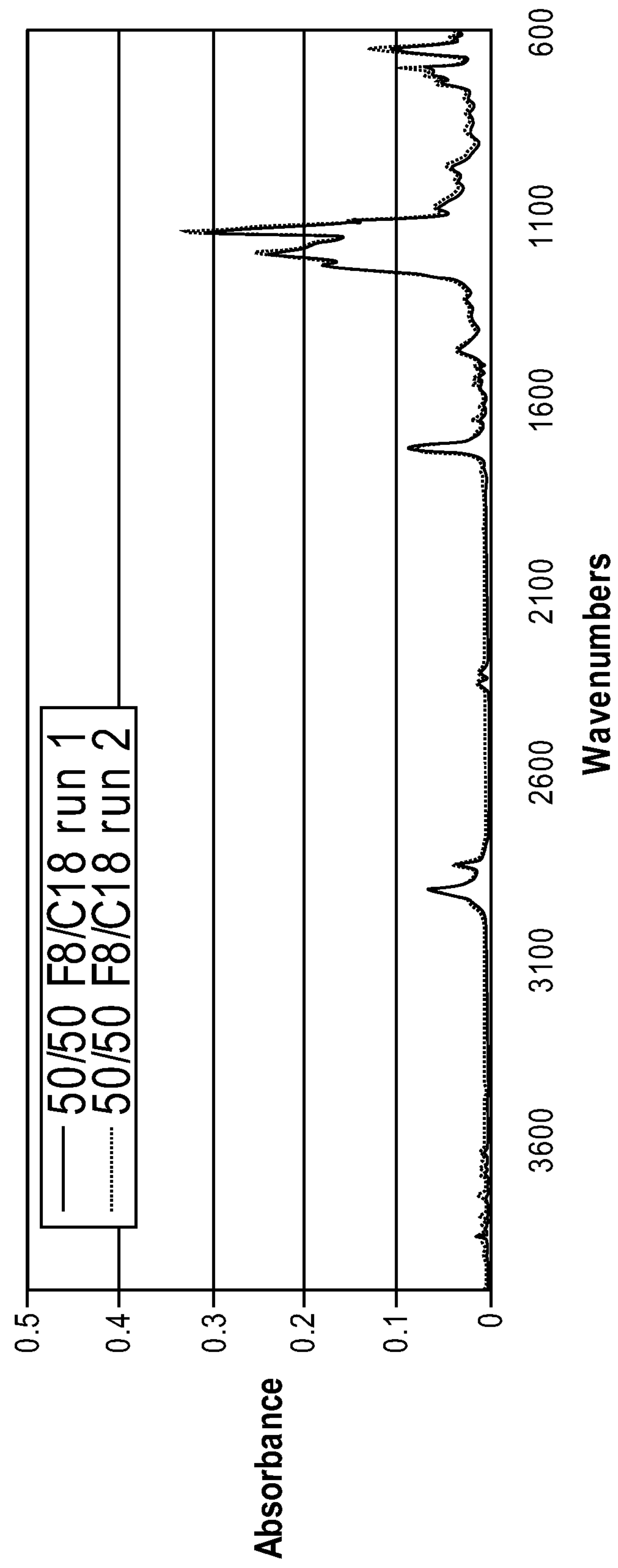
FIG. 3 shows Infrared absorption spectra of the 50/50 F8/$C_{18}$ polymer on PET.
Figure 4:
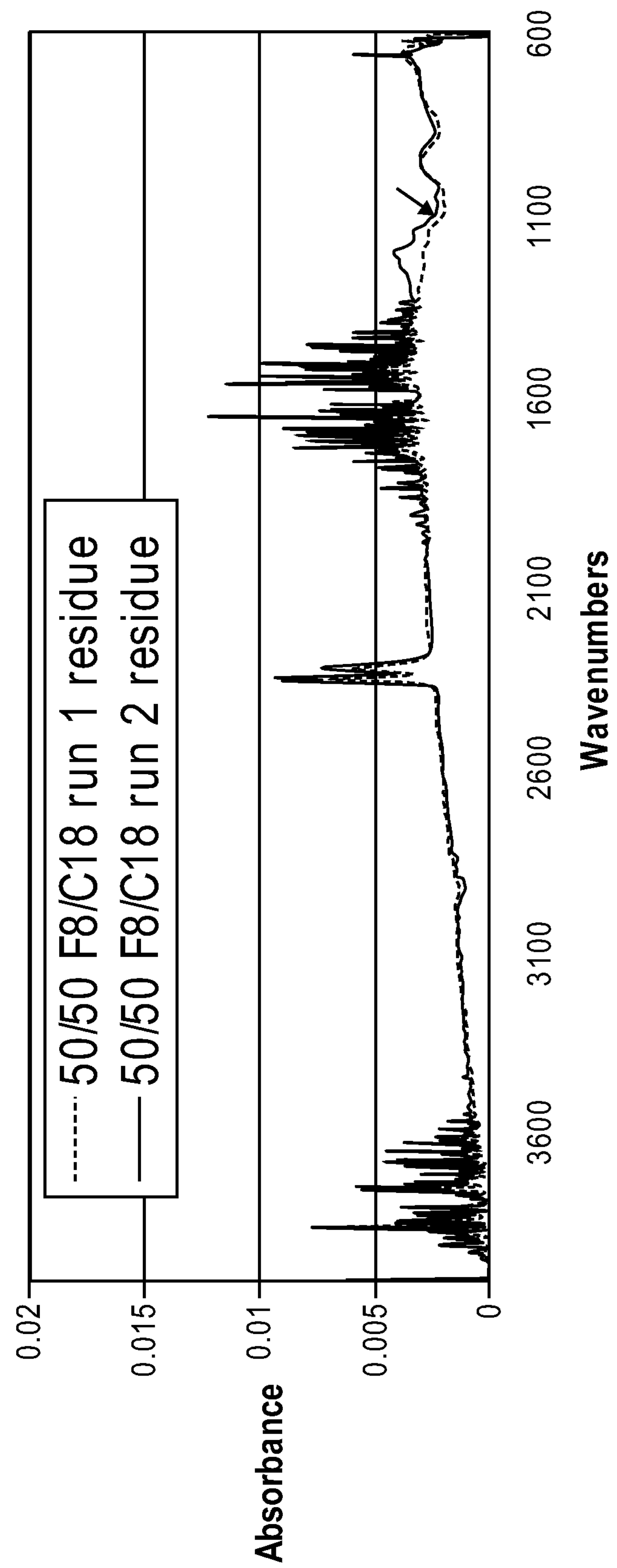
FIG. 4 shows Infrared absorption spectra of the 50/50 F8/$C_{18}$ polymer residue on the FTIR ATR plate after removal of the polymer from the PET of FIG. 3. Note that the y-axis range is much smaller for the residue spectrum of FIG. 4 than for FIG. 3.

Residue analysis was performed to investigate the propensity for material transfer from a coated parting film to pre-preg during lay-up. This test consisted of pressing a material against an FTIR ATR crystal, collecting a 128 scan absorbance spectrum of the material, removing the material, and collecting a 128 scan absorbance spectrum of the residue on the ATR crystal. The spectra of the 50/50 F8/$C_{18}$ polymer on PET pressed against the ATR crystal and the residue after removal are shown in FIGS. 3 and 4, respectively. The negative peaks in FIG. 4 between 2800 $cm^{-1}$ and 3000 $cm^{-1}$ are an artifact from the background subtraction. When FIG. 4 is compared to reference spectra for water vapor and $CO_2$, the water vapor and $CO_2$ peaks explain all features except the very small peak at 1140 $cm^{-1}$ (arrow on FIG. 4) that matches the strongest peak in FIG. 3. The small peak at 1140 $cm^{-1}$ is <1% the intensity of the 1140 $cm^{-1}$ peak in FIG. 3, and thus represents negligible residue.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the intended purpose described herein. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. A thermoresponsive adhesive material comprising:

a linear, phase-separated polymer having fluorinated polymer units and hydrophobic polymer units, the fluorinated polymer units and the hydrophobic polymer units being randomly ordered along the polymer, the hydrophobic polymer units including a first hydrophobic polymer unit and a second hydrophobic polymer unit, the first hydrophobic polymer unit being chosen from acrylate units or methacrylate units each substituted with one or more linear alkyl groups, linear alkenyl groups or combinations thereof, where at least one of the linear alkyl groups or alkenyl groups has 18 to 20 carbon atoms, and wherein the second hydrophobic polymer unit is chosen from acrylate units or methacrylate units each substituted with one or more linear alkyl groups, linear alkenyl groups or combinations thereof, where at least one of the linear alkyl or alkenyl groups of the second hydrophobic polymer unit has 5 to 12 carbon atoms;

wherein a peak adhesive strength of the thermoresponsive adhesive material is modifiable and reversible with a change in temperature.

2. The thermoresponsive adhesive material of claim 1, wherein the fluorinated polymer units are formed from monomers of formula 1:

(1)

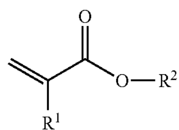

where $R^1$ is a hydrogen or methyl and $R^2$ is a fluoro alkyl having 6 to 20 carbon atoms.

3. The thermoresponsive adhesive material of claim 2 wherein the fluorinated polymer units are formed from monomers of formula 2:

(2)

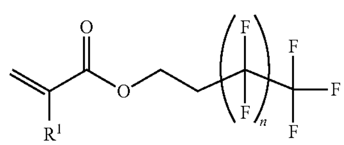

where $R^1$ is a hydrogen or methyl and n ranges from 5 to 17.

4. The thermoresponsive adhesive material of claim 3 wherein the first hydrophobic polymer unit is formed from monomers of formula 3:

(3)

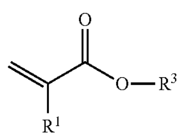

where $R^1$ is a hydrogen or methyl group and $R^3$ is an alkyl or alkenyl having 18 to 19 carbon atoms.

5. The thermoresponsive adhesive material of claim 4 wherein $R^3$ is an alkyl having 18 carbon atoms.

6. The thermoresponsive adhesive material of claim 3, wherein the second hydrophobic polymer unit is formed from monomers of generic formula 4:

(4)

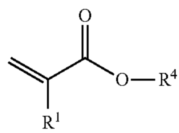

where $R^1$ is a hydrogen or methyl and $R^4$ is an alkyl or alkenyl having 5 to 12 carbon atoms.

7. A method of making a thermoresponsive adhesive material, the method comprising:

combining at least one fluorinated monomer, a first hydrophobic monomer, and a second hydrophobic monomer and heating the monomers to form a linear, phase-separated polymer having fluorinated polymer units and hydrophobic polymer units that are randomly ordered along the phase-separated polymer, the at least one fluorinated monomer being chosen from acrylates or methacrylates each substituted with fluorinated alkyl groups, the first hydrophobic monomer being chosen from acrylates or methacrylates substituted with at least one linear alkyl group, linear alkenyl group or a combination thereof, at least one of the alkyl or alkenyl groups having 18 to 20 carbon atoms, and the second hydrophobic monomer being chosen from acrylates or methacrylates substituted with at least one linear alkyl group, linear alkenyl group or a combination thereof, at least one of the alkyl or alkenyl groups of the second hydrophobic monomer having 5 to 12 carbon atoms; and wherein a peak adhesive strength of the thermoresponsive adhesive material is modifiable and reversible with a change in temperature.

8. The method of claim 7, wherein the at least one fluorinated monomer is a compound of formula 1:

(1)

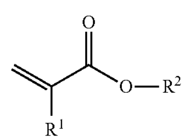

where $R^1$ is a hydrogen or methyl and $R^2$ is a fluoro alkyl having 6 to 20 carbon atoms.

9. The method of claim 7, wherein the at least one fluorinated monomer is a compound of formula 2:

(2)

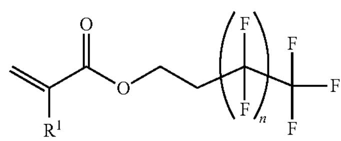

where $R^1$ is a hydrogen or methyl and n ranges from 5 to 17.

10. The method of claim 7, wherein the first hydrophobic monomer is a compound of formula 3:

(3)

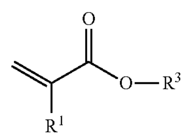

where $R^1$ is a hydrogen or methyl group and $R^3$ is an alkyl or alkenyl having 18 to 19 carbon atoms.

11. The method of claim 10, wherein $R^3$ is an alkyl having 18 carbon atoms.

12. The method of claim 7, wherein the second hydrophobic monomer is a compound of formula 4:

(4)

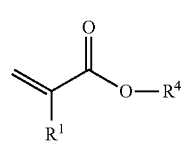

where $R^1$ is a hydrogen or methyl and $R^4$ is an alkyl or alkenyl having 5 to 12 carbon atoms.

13. A method, comprising:

covering a mold tool for a composite part with a parting film, the parting film comprising a polymer sheet and a thermoresponsive adhesive material on the polymer sheet, the thermoresponsive adhesive material having a property of changing adhesion with a change in temperature, the parting film being positioned so that the polymer sheet is between the mold tool and the thermoresponsive adhesive material;

laying up at least one layer of pre-preg on the parting film covering the mold tool to form a composite part, the pre-preg comprising an adhesive surface in contact with the thermoresponsive adhesive material, the thermoresponsive adhesive material resulting in the at least one layer of pre-preg adhering to the parting film with a first adhesion force while laying up occurs;

changing the temperature of the thermoresponsive adhesive material from a first temperature to a second temperature to modify the first adhesion force to a second adhesion force that is less than the first adhesion force; and removing the composite part from the parting film, wherein the thermoresponsive adhesive material comprises a linear, phase-separated polymer having fluorinated polymer units and hydrophobic polymer units, the fluorinated polymer units and the hydrophobic polymer units being randomly ordered along the polymer, the hydrophobic polymer units including a first hydrophobic polymer unit and a second hydrophobic polymer unit, the first hydrophobic polymer unit being chosen from acrylate units or methacrylate units each substituted with one or more linear alkyl groups, linear alkenyl groups or combinations thereof, where at least one of the linear alkyl groups or alkenyl groups has 18 to 20 carbon atoms, and wherein the second hydrophobic polymer unit is chosen from acrylate units or methacrylate units each substituted with one or more linear alkyl groups, linear alkenyl groups or combinations thereof, where at least one of the linear alkyl or alkenyl groups of the second hydrophobic polymer unit has 5 to 12 carbon atoms; and wherein a peak adhesive strength of the thermoresponsive adhesive material is modifiable and reversible with a change in temperature.

14. The method of claim 13, wherein the laying up and the removing the composite part are repeated a plurality of times without removing the parting film from the mold tool.

15. The method of claim 13, wherein the polymer sheet comprises a material chosen from polyethylene, polyethylene terephthalate ("PET"), fluorinated ethylene propylene ("FEP"), nylon and combinations thereof.

16. The method of claim 13, wherein the polymer sheet is a corona-treated polymer sheet to improve adhesion.

17. The method of claim 13, wherein the fluorinated polymer units are formed from monomers of formula 1:

(1)

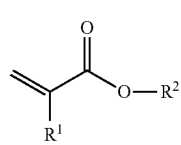

where $R^1$ is a hydrogen or methyl and $R^2$ is a fluoro alkyl having 6 to 20 carbon atoms.

18. The method of claim 13, wherein the fluorinated polymer units are formed from monomers of formula 2:

(2)

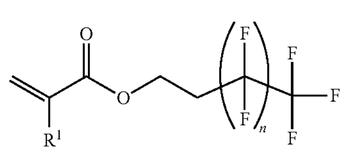

where $R^1$ is a hydrogen or methyl and n ranges from 5 to 17.

19. The method of claim 13, wherein the first hydrophobic polymer unit is formed from monomers of formula 3:

(3)

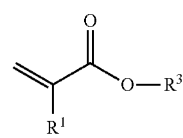

where $R^1$ is a hydrogen or methyl group and $R^3$ is an alkyl or alkenyl having 18 to 19 carbon atoms.

20. The method of claim 19, wherein $R^3$ is an alkyl having 18 carbon atoms.

21. The method of claim 13, wherein the second hydrophobic polymer unit is formed from monomers of generic formula 4:

(4)

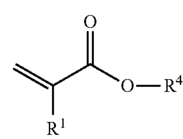

where $R^1$ is a hydrogen or methyl and $R^4$ is an alkyl or alkenyl having 5 to 12 carbon atoms.

22. The method of claim 13, wherein the second temperature is about 1° to about 15° Celsius cooler than the first temperature.

23. The method of claim 13, wherein the adhesive surface of the pre-preg comprises epoxy chemical groups.

24. A method, comprising:

adhering a first object to a second object with a thermoresponsive adhesive material, the thermoresponsive adhesive material having a property of changing adhesion with a change in temperature, the thermoresponsive adhesive material resulting in the first object adhering to second object with a first adhesion force;

changing the temperature of the thermoresponsive adhesive material from a first temperature to a second temperature to reduce the adhesion between the second object and the thermoresponsive adhesive material to a second adhesion force, the second adhesion force being less than the first adhesion force; and removing the first object from the second object, wherein the thermoresponsive adhesive material comprises a linear, phase-separated polymer having fluorinated polymer units and hydrophobic polymer units, the fluorinated polymer units and the hydrophobic polymer units being randomly ordered along the polymer, the hydrophobic polymer units including a first hydrophobic polymer unit and a second hydrophobic polymer unit, the first hydrophobic polymer unit being chosen from acrylate units or methacrylate units each substituted with one or more linear alkyl groups, linear alkenyl groups or a combination thereof, where at least one of the linear alkyl or alkenyl groups has 18 to 20 carbon atoms, and wherein the second hydrophobic polymer unit is chosen from acrylate units or methacrylate units each substituted with one or more linear alkyl groups, linear alkenyl groups or a combination thereof, where at least one of the linear alkyl or alkenyl groups of the second hydrophobic polymer unit has 5 to 12 carbon atoms; and wherein a peak adhesive strength of the thermoresponsive adhesive material is modifiable and reversible with a change in temperature.

25. The method of claim 24, wherein the second adhesion force is 90% less to 100% less than the first adhesion force.

26. The method of claim 24, wherein the first object is a bandage and the second object is a person.

27. A self-adhesive object, comprising:

a flexible substrate; and a thermoresponsive adhesive material on the substrate, the thermoresponsive adhesive material having a property of changing adhesion with a change in temperature, wherein the thermoresponsive adhesive material comprises a linear, phase-separated polymer having fluorinated polymer units and hydrophobic polymer units, the fluorinated polymer units and the hydrophobic polymer units being randomly ordered along the polymer, the hydrophobic polymer units including a first hydrophobic polymer unit and a second hydrophobic polymer unit, the first hydrophobic polymer unit being chosen from acrylate units or methacrylate units each substituted with one or more linear alkyl groups, linear alkenyl groups or a combination thereof, where at least one of the linear alkyl or alkenyl groups has 18 to 20 carbon atoms, and wherein the second hydrophobic polymer unit is chosen from acrylate units or methacrylate units each substituted with one or more linear alkyl groups, linear alkenyl groups or a combination thereof, where at least one of the linear alkyl or alkenyl groups of the second hydrophobic polymer unit has 5 to 12 carbon atoms; and wherein a peak adhesive strength of the thermoresponsive adhesive material is modifiable and reversible with a change in temperature.

28. The self-adhesive object of claim 27, wherein the self-adhesive object is a parting film and the substrate is a polymer sheet comprises a material chosen from polyethylene, polyethylene terephthalate ("PET"), fluorinated ethylene propylene ("FEP"), nylon and combinations thereof.

29. The self-adhesive object of claim 27, wherein the self-adhesive object is a bandage.

* * * * *